United States Patent [19]

Tararine et al.

[11] Patent Number: 5,048,102
[45] Date of Patent: Sep. 10, 1991

[54] MULTIPLE INTERPOLATION PROCESS FOR IMAGE CORRECTION

[75] Inventors: Michel Tararine, Sceaux; Bernard Thevenin, Saint Egreve, both of France

[73] Assignee: Commissariat a l'Energie Atomique, Paris, France

[21] Appl. No.: 244,715

[22] Filed: Sep. 14, 1988

[30] Foreign Application Priority Data

Sep. 16, 1987 [FR] France .................... 87 12814

[51] Int. Cl.$^5$ .............................................. G06K 9/36
[52] U.S. Cl. ........................................ 382/41; 382/44; 382/47
[58] Field of Search ................ 358/426; 382/41, 44, 382/47, 54

[56] References Cited

U.S. PATENT DOCUMENTS

| 4,381,547 | 4/1983 | Ejiri | 382/47 |
|---|---|---|---|
| 4,446,529 | 5/1984 | Strolle | 364/723 |
| 4,484,347 | 11/1984 | Kashioka | 382/47 |
| 4,528,693 | 7/1985 | Pearson et al. | 382/47 |
| 4,578,812 | 3/1986 | Yui | 382/47 |
| 4,610,026 | 9/1986 | Tabata et al. | 382/47 |

FOREIGN PATENT DOCUMENTS 0070677 1/1983 European Pat. Off. .
2026811 2/1980 United Kingdom .

OTHER PUBLICATIONS

Hewlett-Packard Journal (vol. 34, No. 10, Oct. 1983).

*Primary Examiner*—David K. Moore
*Assistant Examiner*—Jose L. Couso
*Attorney, Agent, or Firm*—Cesari and McKenna

[57] ABSTRACT

A multiple interpolation process for image correction involves the precalculation of interpolation contributions relative to all the possible locations of the points of an elementary mesh. The positions of these locations are determined as a function of an interpolation fineness to be obtained. It is shown that this precalculation can be obtained without significantly enlarging the memory of an apparatus used. In addition, the performance speed permits the "in flight" definition of images and the display of weakly defined images in highly defined images.

7 Claims, 3 Drawing Sheets

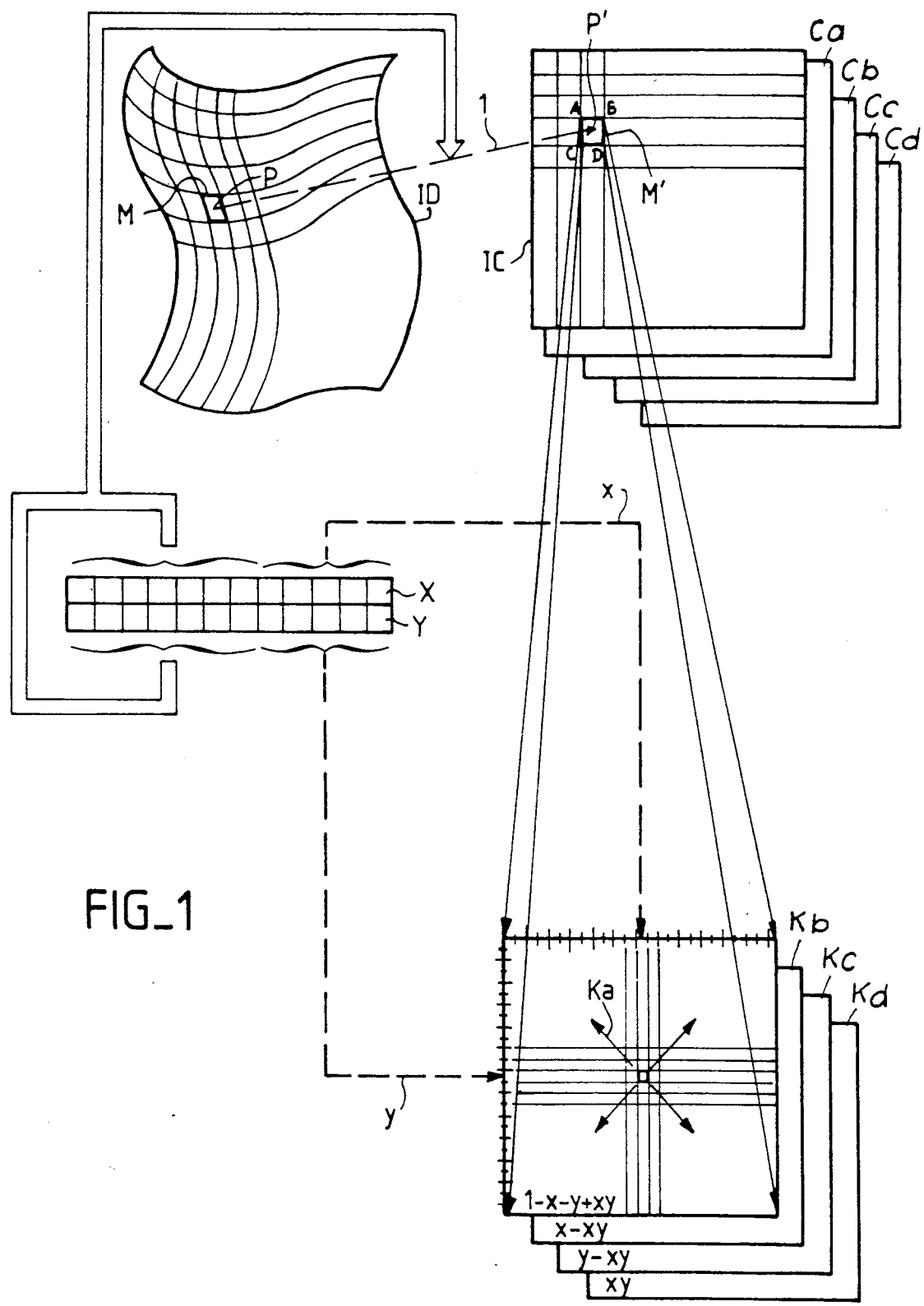
FIG_1

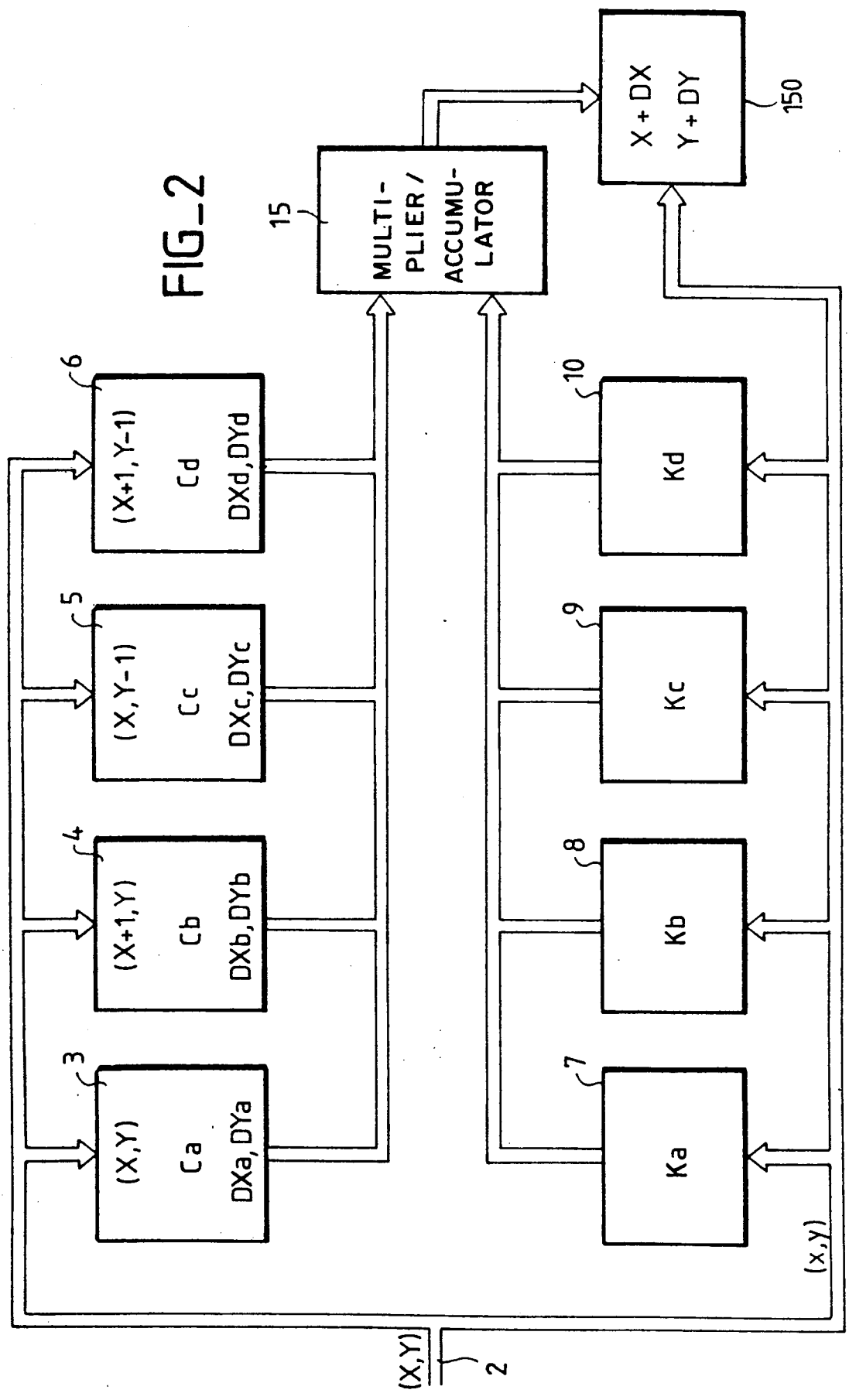

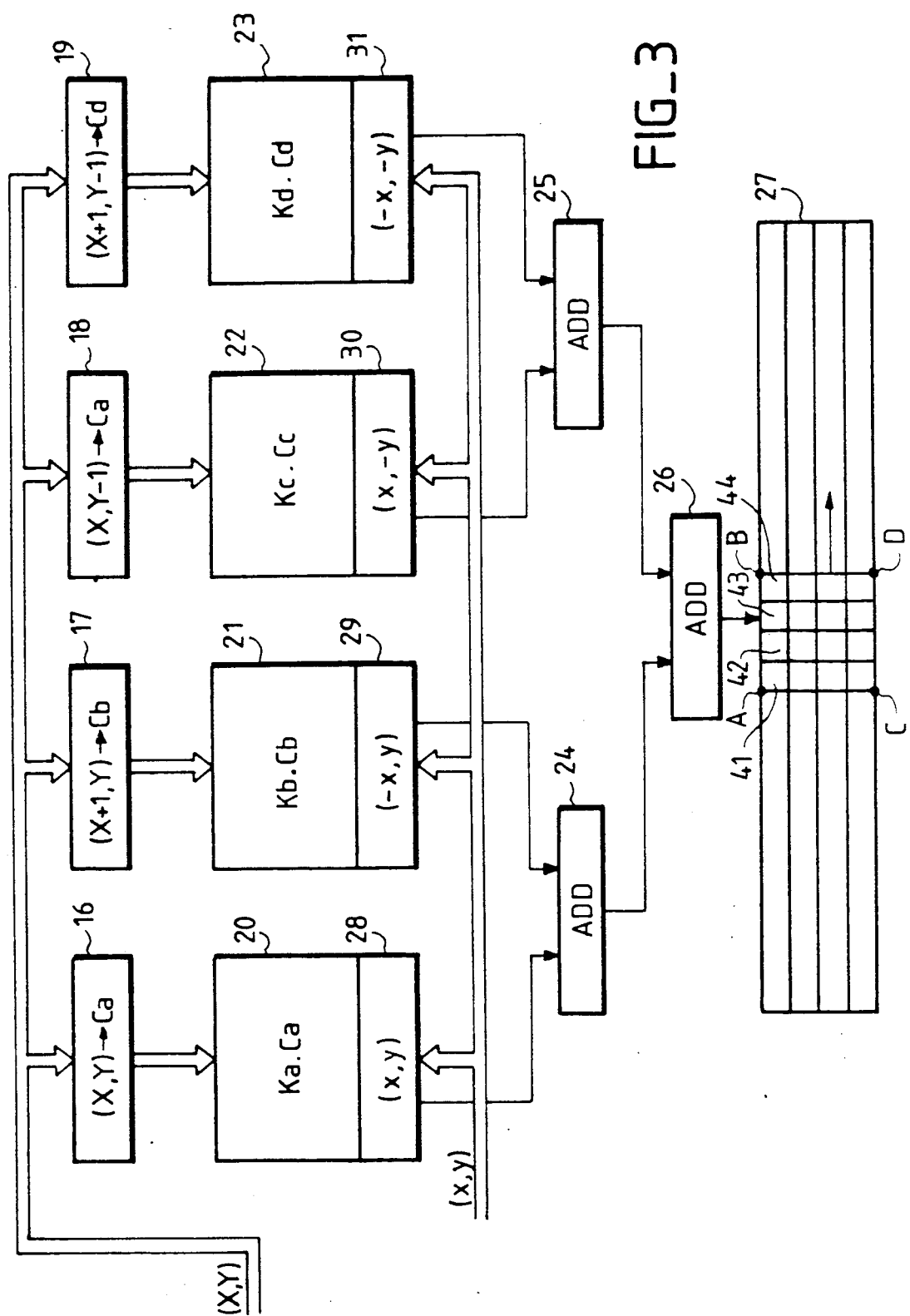
FIG_3

MULTIPLE INTERPOLATION PROCESS FOR IMAGE CORRECTION

The present invention relates to a process for the interpolation of the value of a point in a mesh or network with N nodes, apices or vertices. The studied interpolation is preferably of the bilinear type, although the invention also applies to cases where it is neither linear, nor double and is instead multiple. In the described example the mesh has four nodes, but in certain applications and in particular imaging applications representing three-dimensional objects, the mesh could have a different number of nodes, e.g. three, six or eight. The inventive interpolation process is used in the medical field for correcting distortions of images acquired with gamma cameras. It can also be used in the video field, where it makes it possible the representation of weak definition images, e.g. with 64×64 image elements, as well as high definition images, e.g. with 256×256 image elements. The main interest of the inventive interpolation process is the speed with which interpolation can be carried out. This speed permits real time processing, while respecting the normal video television representation standards for the display of the images.

Gamma cameras are used in nuclear medicine for visualizing in an organ the distribution of molecules marked by a radioactive isotope injected into a patient. A gamma camera generally comprises a collimator for focussing the gamma photons emitted by the patient, a scintillator crystal for transforming the gamma photons into light particles or scintillations and a network of photomultiplier tubes, which bring about a transformation of each of the scintillations into electrical pulses, called electrical contributions of the tubes. They also comprise electronic circuits for producing, on the basis of the electrical contributions supplied by the photomultiplier tubes, signals of coordinates X and Y of the location at which a scintillation has occurred, as well as a validation signal Z when the energy W of the scintillation belongs to a predetermined energy band.

This detection chain is generally followed by a visual display means, which can incorporate a cathode ray oscilloscope controlled by signals of coordinates X,Y and Z for displaying the impact point of the gamma photon on the crystal by a light point or spot on the screen. This impact is also called the image event. The display means can optionally have a photographic apparatus or camera for forming an image of the observed organ, while integrating a large number of light spots produced on the cathode ray screen. It can also comprise a digital processing of the images. In particular, the display means can be adapted to the representation of tomographic images of the organ observed. In order to achieve this objective, several images of said organ are acquired in accordance with a plurality of observation orientations of the gamma camera with respect to said organ. By signal processing operations, identical to those used in computerized tomographs, it is possible to reconstruct images of sections of examined organs.

A gamma camera must have a good spatial resolution, i.e. the capacity to distinguish small radioactive sources which are close together, a good count rate response, i.e. the capacity to process a large number of events per time unit and an image quality which is as independent as possible of the considered isotope energy. The spatial resolution is dependent on the accuracy of the calculations of the coordinates X and Y of each of the image events. The quality of the production of these coordinates is dependent on the accuracy of the measurements and the physical laws governing the operation of the different parts of the gamma camera. Thus, the interaction of a gamma photon with the crystal gives rise to a light scintillation, whose intensity decreases exponentially with time. This scintillation is seen by several photomultiplier tubes simultaneously. The light particles forming said scintillation detach or remove photoelectrons from the photocathodes of the photomultiplier tubes. The number of removed photoelectrons, for a given scintillation obeys the statistical Poisson Law. Moreover, for a constant energy, the electrical contribution is a substantially gaussian function of the distance separating the center of the photomultiplier tube from the projection of the location where the scintillation has occurred. If the scintillation occurs perpendicular to the center of the tube, the electrical contribution is maximum. The further the scintillation from the center of the tube the lower the electrical contribution. For example, if a scintillation occurs perpendicular to the wall of the tube, its electrical contribution is roughly reduced by half compared with the maximum electrical contribution.

A scintillation is seen by several photomultiplier tubes simultaneously and in general by six to ten tubes. In addition, the determination of the location of said scintillation on the crystal, which is itself representative of the emission point of the exciting gamma photon (and therefore the image event), can be obtained by calculating the location of the barycenter of the electrical contribution supplied by all the photomultiplier tubes excited by said scintillation. This calculation takes place in a simple manner, according to the U.S. Pat. No. 3,011,057 (Anger), by injecting electrical contributions across a set of impedance matrixes, whereof the impedance values are a function of the positions of the photomultiplier tubes to which they are connected. The positions of these tubes are referenced with respect to Cartesian reference axles, whereof the intersection point or origin is generally in the center of the network of tubes. In each matrix, there is the same number of impedances as there are photomultiplier tubes in the network of tubes. Each of the impedances is connected, on the one hand, to the output of a different photomultiplier tube and, on the other, to a common point constituting the output of the matrix. Thus, these impedances form a weighting of the electrical contributions of each of the photomultiplier tubes which supply them.

One of the problems caused by gamma cameras of the Anger type is that they have geometrical distortions of the image linked with the light trapping structure: scintillator crystal - photomultiplier tube - barycentering matrix.

Advances in nuclear medicine and, in particular, the improvements made for collecting more information and better information from gamma cameras, e.g. for the detection of small tumors, lead to the optimization of the spatial resolution to the detriment of the characteristic linearity inherent in the design and construction of the cameras. Thus, there is a disturbing spatial distortion of the images, which is the origin of density uniformity defects, which can be of a significant nature. For example, a contraction of 0.4 mm of the radius of the image of a circular surface with a radius of 1 cm leads to a uniformity defect of 8%. These uniformity defects can be particularly disturbing in tomography, where the amplification effect of the uniformity defects due to the reconstruction processes can be higher than a factor of 10.

In the prior art, attempts have been made to correct the effects of said distortion. The general principle of the correction is as follows. The measurement takes place of an image of a regular pattern placed between a uniform emission radioactive source and the gamma camera. If the gamma camera were perfect, the represented image would correspond to the regular distribution of the slits or holes of the pattern.

The measurement carried out shows irregularities due to spatial distortion effects. However, in the thus acquired image, it is possible to use the knowledge of the distortion, measured by comparing the acquired image with the theoretical distribution which should have been obtained, in order to carry out corrections to the images subsequently acquired with the same gamma camera.

In the state of the art, constituted by European Patent 21366, a computer produces a correction matrix of 64×64 new coordinates U and V of an undistorted image corresponding to the same number of coordinates X and Y of the distorted image of the pattern. In the correction operation, the acquired coordinates X and Y of the image events are coded on 12 bits. The 6 most significant bits of X and Y address the memory of U and V. A linear interpolation then takes place using the 6 least significant bits of X and Y. Thus, use is made of the displacement of one image event to be placed with respect to the four angles of the elementary mesh U,V of the corrected image in which the image element must finally be located. Taking account of an image field of approximate diameter 400 mm, a codification on 12 bits of the coordinates of the image events would normally lead to an image definition of approximately 0.1 mm.

It has been shown that this definition can only be obtained in practice if the correction matrix was, in fact, a matrix of 128×128 meshes and, therefore, on using seven most significant bits for determining in which mesh of the corrected image must be located the image event to be positioned. This determination is equivalent to attributing coordinate correction to the nodes of the 128×128 meshes of the acquired image. This being the case, said difference does not in principle influence the present invention. Thus, the representation of images with 128×128 image events is also far two approximate. It is necessary to achieve a finer resolution. Bearing in mind the fact that the acquired coordinates of the image events (of the distorted image) are given on 12 bits, there remain 5 bits for effecting an interpolation of the true position of an image event in the corrected mesh to which it has just been established that it should belong. By interpolation, a calculation takes place of the displacement to be applied to the event, on the basis of the coordinate corrections to be applied to the nodes of the meshes. On calling x and y the coordinates, relative to the least significant bits, of the image element in the acquired mesh, the interpolation consists of determining DX,DY, the displacements to be applied to the position of the event located within a mesh in order to correct it. This correction is dependent on x and y and the way in which the acquired mesh has been transformed in order to become the corrected mesh. If A,B,C and D are the nodes of a square mesh in the acquired image, said nodes with the distortion correction must respectively be transformed, i.e. must undergo coordinate corrections DXa-DYa, DXb-DYb, DXc-DYc and DXd-DYd along the two reference axes of the image. These coordinate corrections are stored in a so-called correction memory.

The distortion correction of the position of the image event to be replaced is then given by the following formulas:

$$DX = (1-x-y+xy)DXa + (x-xy)DXb + (y-xy)DXc + (xy)DXd$$

$$DY = (1-x-y+xy)DYa + (x-xy)DYb + (y-xy)DYc + (xy)DYd$$

The conventional method for calculating the interpolation, for the calculation of each displacement DX or DY, passes through two intermediate calculation levels. There is firstly a calculation of a first correction CI on the basis of the coordinates x (or respectively y) and corrections of coordinates of the two nodes of the mesh : DXa (or DYa) and DXb (or DYb). With two accesses to the memory where the coordinates of the nodes of the corrected meshes are stored, this gives an intermediate result CIx (or CIy). This is followed by a calculation of another correction CJ by interpolation between the two other nodes C and D of the mesh. CJx (or CJy) is obtained in a corresponding manner with two other accesses to the memory. On the basis of CI and CJ, the final calculation consists of obtaining the displacement DX (or DY). Thus, to obtain each of the image displacements of an image event in the corrected image, there are four memory accesses (at A,B,C and D), four multiplications taking account of the coordinates x (or y), two additions for determining CI and CJ, two accesses to the intermediate values CI and CJ, two further multiplications taking account of the coordinates y (or x) and finally an addition for obtaining the final displacement DX (or DY). These numerous operations are prejudicial to the speed of the presentation of the corrected images.

When the number of least significant bits to be interpolated is not very large, e.g. 3 bits, it is possible to precalculate for each corrected mesh the definitive corrections which must be attributed to image events placed within the acquired meshes. There is then a direct addressing in order to obtain the pre-interpolated values. As the determination of the corrected mesh has itself been obtained by addressing, said procedure amounts to carrying out a direct addressing of the complete correction. However, this procedure suffers from a disadvantage, namely that it is unusable in the case of an excessive number of addressing bits. This means that it is unusable if the accuracy of the expected resolution of the image is too great or, which amounts to the same thing, if the interpolation has to be carried out on an excessive number of bits. Thus, when the coordinates are given on 12 bits, any image correction process definitively based on such a direct addressing method requires an exorbitant memory capacity. In particular, for an image with 4096×4096 image points, it would be necessary to have a memory with 16 megawords of 24 bits (12 bits for determining the corrected X and 12 bits for determining the corrected Y). This memory would be addressed by the X and Y acquired and coded in each case on 12 bits. This capacity exceeds the presently available technological limits.

The invention aims at obviating these disadvantages by proposing an interpolation process in which the memory capacity is not particularly increased, but where the interpolation calculation can be carried out in real time. The fact that the interpolation calculation can be carried out in real time can be used in the video field. Thus, the representation of movement requires the acquisition and storage of numerous elements. In order not to excessively increase the memory capacity at the time of said storage, it can be useful, in view of the fact that only movement is of interest, to only store degraded definition images. In certain cases, particularly when studying cardiac movements by gamma camera, the images obtained have from the outset a low definition. However, at the time of the display, it may be necessary to reduce the brightness level differences and to increase the resolution of the image by recreating, on the basis of images stored in small numbers in the memory (limited resolution) high resolution images (introduction of intermediate image events into each stored image event mesh) and with an enriched grey level number. However, intermediate image events can only be created to the extent that it is possible to give to them intermediate grey levels within the same grey level range. Thus, the reduction of the light transitions only occurs if the grey level variation between adjacent image elements in the weakly defined image is large. The real time calculation permitted by the invention then makes it possible to produce such high definition images "in flight" on the basis of low definition images stored in large numbers.

Therefore, the invention relates to a process for the multiple interpolation of the value of a point, in a mesh with N nodes, characterized in that it involves the following stages:

determining an interpolation fineness to be obtained, the precalculation of the interpolation contributions relative to all the possible locations of the mesh for the given fineness and as a function of the coordinates of these locations in said mesh, and to the point is attributed as the interpolated value, the result of an algebraic composition of the contributions, relative to the coordinates of the point in the mesh, and weighting coefficients of the nodes of the mesh.

The invention is described in greater detail hereinafter relative to non-limitative embodiments and the attached drawings, wherein show:

FIG. 1 a functional diagrammatic representation of the inventive interpolation process.

FIG. 2 a functional diagram of the means used in the inventive process.

FIG. 3 a preferred variant of the preceeding diagram in an application of the video type.

FIG. 1 diagrammatically represents the interpolation process according to the invention. A point P, or image event, is defined, following acquisition, by its coordinates X and Y. In a preferred embodiment, the acquisition is obtained as a result of an experiment with a gamma camera and the coordinates X and Y are given in binary form with 12 definition bits. Point P belongs to an unusable distorted image ID. In order to be usable, said image must be corrected by an image distortion correction process. It is necessary to calculate the coordinates of a point P' in a corrected image IC. In distortion correction processes, to each elementary mesh M of the distorted image ID acquired is attributed a corrected mesh M', whose nodes A,B,C and D are defined by coordinate corrections, which are also referred to here as weighting coefficients DXa - DYa, DXb . . . DYd. By determining the resolution of the correction mesh system, it is possible to carry out a distortion correction in two periods. A first consists of attributing a mesh M' to a mesh M. The second consists of interpolating the position of point P' in mesh M' as a function of the position of the point P in mesh M and as a function of the weighting coefficients of the nodes of the mesh. Arrow 1 represents the first operation. Use is made of the most significant bits of coordinates X and Y. In a particular realization, use is made of seven most significant bits in order to obtain a mesh system of 400×128 meshes in the distorted images ID and corrected images IC.

The interpolation fineness to be obtained is determined in the present invention. In the represented example, the interpolation fineness to be obtained relates to the five least significant bits, designated x and y, of coordinates X and Y. If Ka is the contribution $(1-x-y+xy)$, Kb the contribution $(x-xy)$, Kc the contribution $(y-xy)$ and Kd the contribution $(xy)$, the invention aims at precalculating the contributions of Ka,Kb,Kc and Kd for all possible values of x and y corresponding to the interpolation fineness to be obtained. These values are then stored in read-only memories, called interpolation matrixes. In the present case, this fineness is measured on five bits, each coordinate x or y thus being able to assume 32 values. By addressing preprogrammed memories containing the different contributions Ka,Kb,Kc and Kd by the coordinates x and y, it is possible to directly obtain the values of the functions representative of these contributions Subsequently DX and DY are determined by applying the following formulas:

$$DX = Ka.DXa + Kb.DXb + Kc.DXc + Kd.DXd$$

$$DY = Ka.DYa + Kb.DYb + Kc.DYb + Kd.DYd$$

As x and y are here coded on five bits in each case, each read-only memory Ka, Kb, Kc and Kd has 1024 storage locations. In practice, each storage location has a contribution coded on eight bits and there are four interpolation matrixes. In other words, the interpolation requires storage increase of 4 Kbytes for storing all the relative contributions Bearing in mind the fact that the correction meshing system has eight storage or memory zones, called coordinate corrections and relative to the displacements of the nodes of the meshes: DXa, DYa, DXb . . . DYd, due to the fact that these coordinate corrections are each coded on eleven bits (one sign bit, eight significant bits, and two fractional bits) and the fact that the correction meshing system is relative to a resolution of 128×128, the overall memory size is twice 16K words of 11 bits of the random-access memory and 4K bytes of the read-only memory. Thus, the coordinate corrections must be able to change, as a function of e.g. the ageing of the gamma camera, whereas the precalculated relative contributions are unchangeable. They can therefore be stored in a read-only memory.

The supplementary memory size for the interpolation matrixes is consequently negligible. It is useful to know that the precalculation of the interpolation contributions can be simplified by using, for the programming of memories Ka, Kb and Kc, the results obtained for the precalculation of memory Kd. The multiplication x.y has not been repeated.

FIG. 2 shows the preferred method of determining the corrected coordinates of point P' in mesh M'. A bus 2 carries the coordinates X and Y up to the coordinate correction memories 3 to 6 on the one hand and to the interpolation memories 7 to 10 on the other. A multiplier - accumulator 15 connected to the outputs of said memories then receives from the correction memories the coordinate correction DX (or DY), on the one hand, and from the interpolation memories 7 to 10 the relative interpolation contributions K, on the other. It performs corresponding multiplications and the accumulation of the results of these multiplications. As a function of the particular case, it supplies the displacement DX and then the displacement DY. Processing is carried out in series with the multiplier - accumulator 15. A correction circuit 150 then supplies the corrected coordinates of the image events by adding the calculated displacements to the distorted coordinates.

Added to the fact that the memory size has been only slightly increased, the inventive process also makes it possible to save time. Thus, the addressing of the coordinate corrections of the different nodes of the correction mesh M' can be simultaneous. Thus, X and Y, or at least the 7 most significant bits of X and Y represent the node A of the mesh. Nodes B,C and D are deduced therefrom by the addition or subtraction of a least significant bit unit from among the most significant bits. Consequently, it is possible to simultaneously ave access to the 8 weighting coefficients DXa, DYa, etc. At the same time, it is possible to simultaneously have access to the contributions Ka,Kb,Kc and Kd. By then replacing the multiplier - accumulator 15 by a set of four multipliers respectively allocated to memories 3 and 7, 4 and 8, 5 and 9 and 6 and 10 and by connecting them to an adder, it is possible to speed up the calculations of the displacements. Thus, during a clock cycle following that when the memories were addressed, it is possible, by means of the multipliers, to carry out each of the multiplications K.DX (or K.DY). During the third cycle period, the displacement values DX (or DY) are available. Three cycle periods later, the other displacement values DY (or DX) is available. It is even possible to have two displacement values simultaneously by further doubling the number of multipliers.

The video application shown in part in FIG. 3 is similar. In the latter, a frame of an available image has a low resolution. For example, it involves 64 rows and 64 columns and there are 4K possible positions of the image events and in exemplified manner each image element can be coded on 8 bits, i.e. 256 grey, luminance or chrominance levels. Therefore, the storage of the images is not very demanding. The reconstruction "in flight" of a more finely defined image, e.g. of $256 \times 256$ makes it necessary to calculate the grey level at 16 locations of a mesh of the mesh system $64 \times 64$. In other words, a mesh referenced by four adjacent nodes belonging to two adjacent lines of the stored image must be broken down into $4 \times 4 = 16$ parts. The coordinate x coded on 2 bits must be able to assume the value 1 to 4 and the coordinate y also coded on 2 bits must be able to also assume the values 1 to 4. Knowing the grey level, the weighting coefficients Ca,Cb,Cc and Cd in each of the nodes A,B C and D of the mesh, it is possible by a calculation similar to that referred to hereinbefore, to calculate the intermediate grey levels of the intermediate points contained in the mesh.

However, in an improvement of the invention, it has been found that rather than only calculate the contributions Ka,Kb,Kc and Kd, it was preferable and possible to carry out the precalculation of all the necessary multiplications. Thus, in view of the fact that the grey levels are only given for each point on 8 bits (256 levels), it is possible to replace the interpolation memories Ka, Kb, Kc and Kd having 16 storage locations (16 possible positions in the mesh) by composite interpolation memories with $16 \times 256$ memory locations. The precalculation carried out in the composite memories is performed on 8 bits.

The sudden grey level transitions between adjacent image elements of the poorly defined image are then reduced by the introduction of intermediate image elements, whereof the grey levels are fixed at intermediate levels in the same grey level range as those of adjacent image elements.

In a first phase of this rapid processing, low definition source images are read for each time cycle in order to determine the grey levels, or weighting coefficients, Ca to Cd of the four mesh nodes A to D. The source memory can be quadrupled in such a way as to be simultaneously addressed at X and Y for simultaneously supplying the weighting coefficient Ca to Cd. In such a way as to avoid the cost imposed by quadrupling the memory, a different organization can be adopted by separating the even image events in x and y. This different organization then makes it possible to simultaneously read, but in different zones of said memory, the weighting coefficients Ca to Cd of the four nodes of the mesh. If necessary, there can also be a reading multiplexing of said memory. The source image memory, or for simplifying the explanation, the source memories 16 to 19 then supply the four weighting coefficients on 8 bits each representing the grey level of one of the mesh nodes. These grey levels can be used as the address input for each of the composite precalculation memories 20 to 23 having effected the product K.C and receiving as another address codes corresponding successively to each of the four intermediate positions of the interpolated points 41 to 44 located on the same line, in the mesh. In one line y is fixed and only x varies (from 1 to 4). The composite memories 20 to 23 then supply in each case successively 4 results corresponding to the calculation of the weighted brightness at four locations in the mesh, as a function of one of the nodes of said mesh. For each location, a set of adders 24 to 26 makes it possible to add the results supplied by the four memories 20 to 23 and to supply the weighted brightness corresponding to said point. With a reading time cycle of 166 nanoseconds, the four brightnesses can be interpolated in 664 nanoseconds. The brightnesses at 256 points of a video line can consequently be calculated in 43 microseconds. The display of the image can then be obtained in the standard video mode. Thus, in standard video reading with 25 images per second, the reading of a line of an image takes 64 microseconds. The compatibility of these two periods (64 microseconds exceeding 43 microseconds) makes the thus presented interpolation process suitable for the "in flight" display of weakly defined images in highly defined images.

The precalculations of the composite memories also has a special feature. On accepting $x=0$ and $y=0$ for the center of a mesh, it can be seen that the composite contribution attributed to a point can be simplified. It is sufficient to only calculate a single composite memory and to make four copies thereof. Only the addressing values used for giving access to these composite memories change. As a function of the envisaged composite contribution, as a function of the node, addresses x and y undergo inversions of values $-x$ and $-y$. This manner of proceeding is of interest. During production there is no need to worry about any random differentiation between the memories 20 to 23. Only the respective access decoders 28 to 31 are thus specified as a function of their object.

The interpolation mode recommended in these two applications is preferably a linear mode. Bearing in mind that it is wished to represent bidimensional images, the interpolation mode will be bilinear. However, the invention can be used for interpolating a point in a three-dimensional geometrical space or even in a theoretical space with M dimensions. In addition, the interpolation is not necessarily linear. Functions other than the linear function can be envisaged. In the case of a mesh with N nodes, it may simply be necessary for the sum of the relative contributions of each of the nodes to be equal to 1.

Moreover, the definition of a mesh with N nodes must not only be considered in the case where N is equal to four, as described hereinbefore. In the case where the mesh has a different form, e.g. triangular or hexagonal, the number of nodes can differ. In these latter cases, rather than calculate the contributions according to a Cartesian definition, it may be preferable to use a polar definition.

We claim:

1. A process for the multiple interpolation of the value of a point P in an elementary mesh A,B,C,D having Cartesian coordinate axes and at least four nodes, from scintillation data produced by a gamma camera and representing an image constituted by picture elements, in order to correct distortions of said image, said process comprising the steps of determining an interpolation fineness to be obtained, precalculating the interpolation contributions relative to all the locations in the mesh for the given fineness and as a function of the coordinates of the said locations in said mesh, attributing to the point P as the interpolated value, the result of an algebraic composition of the contributions relative to the coordinates of the point and weighting coefficients $Ca, Cb, Cc, Cd$ of the mesh nodes, that composition being of the form $Ka \cdot Ca(x,y) + Kb \cdot Cb(x,y) + Kc \cdot Cc(x,y) + Kd \cdot Cd(x,y)$, being stored and determining therefrom the displacement value of said point P, outputting a corrected image.

2. The process according to claim 1, wherein the multiple interpolation is a double interpolation x and y.

3. The process according to claim 2, wherein the double interpolation is a bilinear interpolation.

4. The process according to claim 1, wherein the interpolated value represents the displacement of a pint to be interpolated measured along an axis.

5. The process according to claim 1, wherein the interpolated value represents the luminance or chrominance of an image element.

6. The process according to claim 5, wherein there is a partial precalculation of the interpolated value as a function of predetermined values of the weighting coefficient.

7. The process according to claim 6, wherein the precalculation of the interpolation contributions involves a composite precalculation of a contribution set and a multiplexing x,-x,y,-y of the addressing of these contributions.

* * * * *